US010967062B2

(12) United States Patent
Panyam et al.

(10) Patent No.: US 10,967,062 B2
(45) Date of Patent: Apr. 6, 2021

(54) FUNCTIONALIZED NANOPARTICLES AND METHODS OF USE THEREOF

(71) Applicant: REGENTS OF THE UNIVERSITY OF MINNESOTA, Minneapolis, MN (US)

(72) Inventors: Jayanth Panyam, Minneapolis, MN (US); Tanmoy Sadhukha, Minneapolis, MN (US); Ameya Kirtane, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/841,145

(22) Filed: Dec. 13, 2017

(65) Prior Publication Data

US 2018/0243423 A1 Aug. 30, 2018

Related U.S. Application Data

(63) Continuation of application No. 13/755,746, filed on Jan. 31, 2013, now abandoned.

(60) Provisional application No. 61/593,707, filed on Feb. 1, 2012.

(51) Int. Cl.
*A61K 47/50* (2017.01)
*A61K 47/69* (2017.01)
*A61K 47/42* (2017.01)
*A61K 47/62* (2017.01)
*A61K 49/00* (2006.01)

(52) U.S. Cl.
CPC .............. *A61K 47/42* (2013.01); *A61K 47/62* (2017.08); *A61K 47/6937* (2017.08); *A61K 49/0093* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,648,071 A * | 7/1997 | Hunter ................. | A61K 31/765 424/78.31 |
| 5,792,742 A | 8/1998 | Gold et al. | |
| 2004/0057947 A1 * | 3/2004 | Duettmann ............ | A61K 33/06 424/94.64 |
| 2008/0038361 A1 | 2/2008 | Cheon et al. | |
| 2008/0187595 A1 | 8/2008 | Jordan et al. | |
| 2008/0247943 A1 | 10/2008 | Lanza et al. | |
| 2009/0291133 A1 | 11/2009 | Wang et al. | |
| 2010/0104645 A1 | 4/2010 | Ali et al. | |
| 2011/0165064 A1 | 7/2011 | Ruoslahti et al. | |
| 2011/0262347 A1 | 10/2011 | Ruoslahti et al. | |
| 2013/0195752 A1 | 8/2013 | Panyam et al. | |

FOREIGN PATENT DOCUMENTS

| | | |
|---|---|---|
| WO | 1996020698 A2 | 7/1996 |
| WO | 2008071679 A1 | 6/2008 |
| WO | 2011043980 A1 | 4/2011 |

OTHER PUBLICATIONS

Kunamneni, Adinarayana, Thaer Taleb Abed Abdelghani, and Poluri Ellaiah. "Streptokinase—the drug of choice for thrombolytic therapy." Journal of thrombosis and thrombolysis23.1 (2007): 9-23. (Year: 2007).*
Global Use of Strategies to Open Occluded Coronary Arteries (GUSTO III) Investigators. A comparison of reteplase with alteplase for acute myocardial infarction. New England Journal of Medicine. Oct. 16, 1997;337(16):1118-23. (Year: 1997).*
Alkjaersig, et al., "The mechanism of clot dissolution by plasmin", J Clin Invest 38, 1086-1095 (1959).
Baxter, et al., "Transport of fluid and macromolecules in tumors. I. Role of interstitial pressure and convection", Microvasc Res 37, 77-104 (1989).
Bi, et al., "Chemical conjugation of urokinase to magnetic nanoparticles for targeted thrombolysis", Biomaterials 30, 5125-5130 (2009).
Diop-Frimpong, et al., "Losartan inhibits collagen I synthesis and improves the distribution and efficacy of nanotherapeutics in tumors", PNAS 108(7), 2909-2914 (2011).
Eikenes, et al., "Collagenase increases the transcapillary pressure gradient and improves the uptake and distribution of monoclonal antibodies in human osteosarcoma xenografts", Cancer Res. 64, 4768-4773 (2004).
Gaffney, et al., "Fibrin-targeted perfluorocarbon nanoparticles for targeted thrombolysis", Nanomedicine 2, 533, 11 pages (2007).
Guedan, et al., "Hyaluronidase expression by an oncolytic adenovirus enhances its intratumoral spread and suppresses tumor growth", Mol Ther 18(7), 1275-1283 (2010).
Ji, et al., "Maleimide Functionalized Poly(ε-caprolactone)-b-poly(ethylene glycol) (PCL-PEG-MAL): Synthesis, Nanoparticle Formation, and Thiol Conjugation", Macromol Chem Phys 210, 823-831 (2009).
Kato, et al., "Collagenase-1 injection improved tumor distribution and gene expression of cationic lipoplex", Int. J. Pharm. 423, 428-434 (2012).

(Continued)

Primary Examiner — Nissa M Westerberg
(74) Attorney, Agent, or Firm — Viksnins Harris Padys Malen LLP

(57) ABSTRACT

Certain embodiments of the present invention provide functionalized nanoparticles and methods of use thereof. Certain embodiments provide nanoparticles functionalized with streptokinase. Certain embodiments of the present invention provide methods for treating a pathological fibrin associated disorder (e.g., cancer) in an animal.

24 Claims, 10 Drawing Sheets

(56) References Cited

OTHER PUBLICATIONS

Li, et al. "PEGylated PLGA nanoparticles as protein carriers: synthesis, preparation and biodistribution in rats", Journal of Controlled Release 71(2), 203-211 (2001).
Ma, et al., "Combination of antiangiogenesis with chemotherapy for more effective cancer treatment", Mol Cancer Ther 7 (12), 3670-3684 (2008).
Patil, et al., "Nanoparticle-mediated simultaneous and targeted delivery of paclitaxel and tariquidar overcomes tumor drug resistance", J Control Release 136, 21-29 (2009).
Patil, et al., "Single-step surface functionalization of polymeric nanoparticles for targeted drug delivery", Biomaterials 30, 859-866 (2009).
Schafer, et al., "Cancer as an overhealing wound: an old hypothesis revisited", Nat Rev Mol Cell Biol 9, 628-638 (2008).
Tlsty, et al., "Tumor Stroma and Regulation of Cancer Development", Annu Rev Pathol Mech Dis 1, 119-150 (2006).
Toti, et al., "Interfacial activity assisted surface functionalization: a novel approach to incorporate maleimide functional groups and cRGD peptide on polymeric nanoparticles for targeted drug delivery", Mol Pharm 7 (4), 1108-1117 (2010).
Trafton, et al., "Removable 'cloak' for nanoparticles helps them target tumors", http://web.mit.edu/newsoffice/2011/cancer-nanoparticle-hammond-0429.html?tmpl=compo, 2 pages (2012).
Wong, et al., "Multistage nanoparticle delivery system for deep penetration into tumor tissue", Proc Natl Acad Sci 108 (6), 2426-2431 (2011).
Yasunaga, et al., "New concept of cytotoxic immunoconjugate therapy targeting cancer-induced fibrin clots", Cancer Sci 102, 1396-1402 (2011).

\* cited by examiner

Lower Chamber $*p < 0.1$

Figures 8A-C
Figure 8A. Blank NP
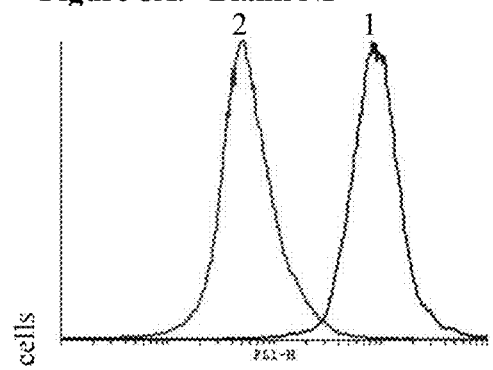
Figure 8B. SK NP
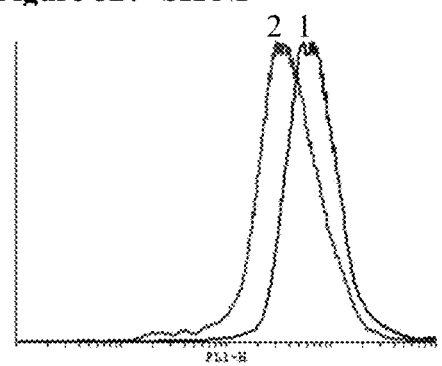
Figure 8C. Blank NP + Free SK
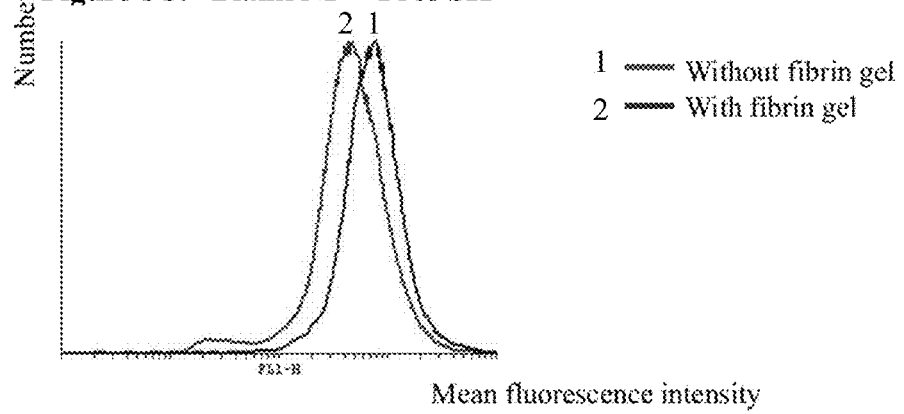
1 ——— Without fibrin gel
2 ——— With fibrin gel
Mean fluorescence intensity

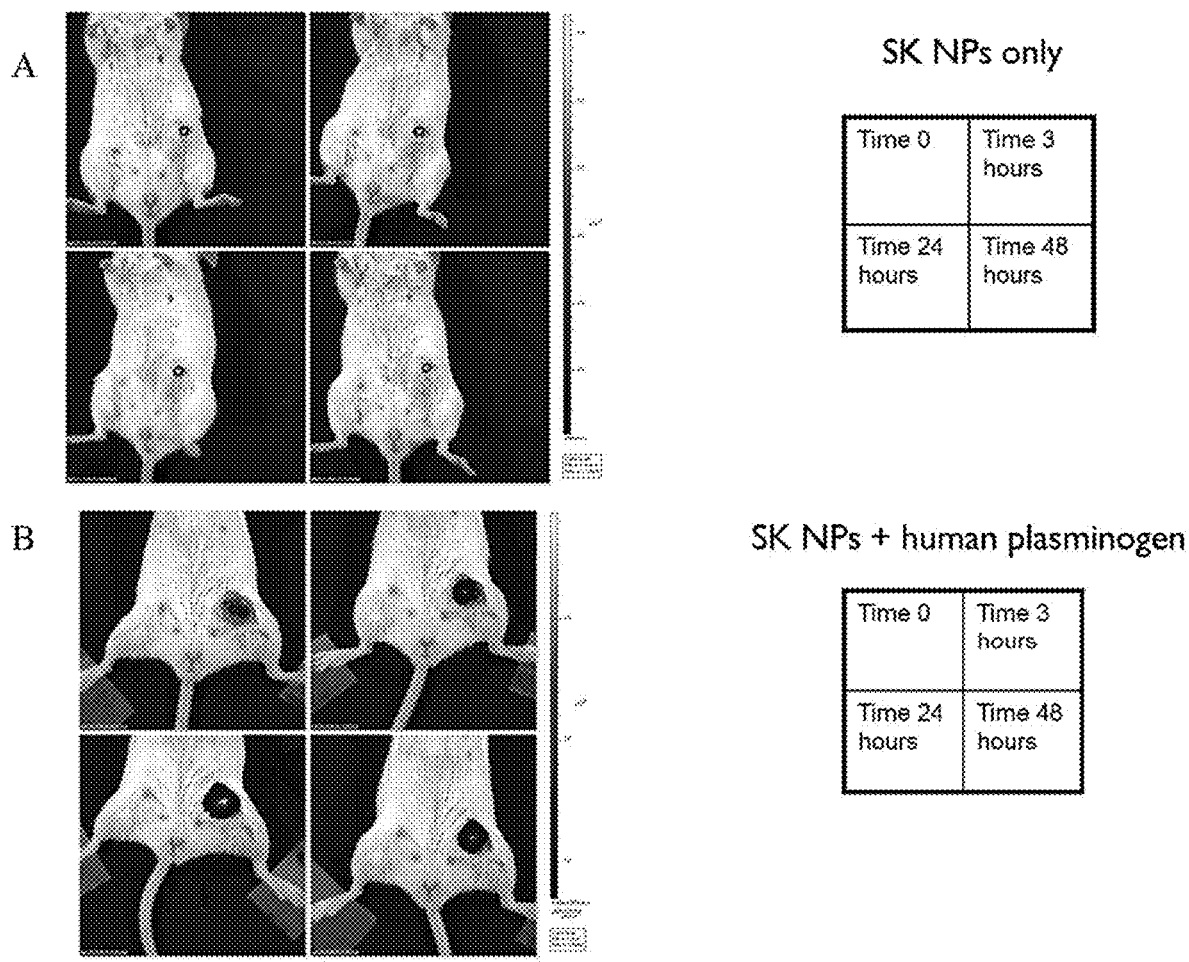
Figures 9A-B

FUNCTIONALIZED NANOPARTICLES AND METHODS OF USE THEREOF

RELATED APPLICATION

This application is a continuation of U.S. application Ser. No. 13/755,746, filed Jan. 31, 2013, which is claims the benefit of U.S. Provisional Application Ser. No. 61/593,707 filed on Feb. 1, 2012, which applications are herein incorporated by reference.

BACKGROUND OF THE INVENTION

Inefficient transport of drug delivery systems through tumor extracellular matrix (ECM) severely limits therapeutic efficacy. Tumors are characterized by the presence of a neo-vasculature that is underdeveloped and leaky. This leads to deposition of fibrin, a key ingredient of blood clot, within the tumor matrix (M. Schafer, S. Werner, *Nat Rev Mol Cell Biol* 9, 628 (2008)). The presence of fibrin is an important cause of elevated interstitial fluid pressure (IFP) in tumors (J. Ma, D. J. Waxman, *Mol Cancer Ther* 7, 3670 (2008)). Elevated IFP, in turn, results in increased resistance to convective transport of drug carriers in the tumor matrix and decreases the amount of drug reaching tumor cells (L. T. Baxter, R. K. Jain, *Microvasc Res* 37, 77 (1989)). This is especially true for central regions of the tumor, which are typically under-perfused. This is a critical problem because these poorly-perfused regions (which have low pH and low $pO_2$) harbor the most aggressive and drug-resistant tumor cells.

Accordingly, there is a need for agents and methods that are useful for treating or preventing cancer. Additionally, there is a need for anti-cancer agents with improved therapeutic efficacy, e.g., improved transport of drug delivery systems through the ECM.

SUMMARY OF THE INVENTION

Certain embodiments of the invention provide a nanoparticle covalently attached directly or indirectly through a linker to one or more moieties independently selected from streptokinase (kabinkinase, streptase), urokinase (abbokinase), arvin, brinase, tissue plasminogen activator (tPA), recombinant tissue plasminogen activator (r-tPA), nattokinase, lumbrokinase, serrapeptase, prourokinase, reptilase, anisoylated purified streptokinase activator complex (AP-SAC), thrombinase, anistreplase (eminase) and staphylokinase.

Certain embodiments of the invention provide a compound of formula (I):

A-B-C-D                                                 (I)

wherein A is poly-lactic acid or and poly-(lactic-co-glycolic acid); B is poly-(ethylene glycol) or poly-(ethylene oxide); C is methyl and D is absent; or C is a linking group and D is one or more moieties independently selected from streptokinase (kabinkinase, streptase), urokinase (abbokinase), arvin, brinase, tissue plasminogen activator (tPA), recombinant tissue plasminogen activator (r-tPA), nattokinase, lumbrokinase, serrapeptase, prourokinase, reptilase, anisoylated purified streptokinase activator complex (AP-SAC), thrombinase, anistreplase (eminase) and staphylokinase.

Certain embodiments of the invention provide a nanoparticle comprising poly-(lactic-co-glycolic acid) and one or more units of formula (I) as described herein.

Certain embodiments of the invention provide a compound or nanoparticle as described herein.

Certain embodiments of the invention provide a pharmaceutical composition comprising a nanoparticle or compound as described herein and a pharmaceutically acceptable carrier.

Certain embodiments of the invention provide a method of delivering a therapeutic agent to an animal in need thereof, comprising administering to the animal a nanoparticle as described herein.

Certain embodiments of the invention provide a method of delivering an imaging agent to an animal in need thereof, comprising administering to the animal a nanoparticle as described herein.

Certain embodiments of the invention provide a method for treating a pathological fibrin associated disorder in an animal, comprising administering to the animal a nanoparticle or compound as described herein. In certain embodiments, the pathological fibrin associated disorder is cancer. In certain embodiments, the pathological fibrin associated disorder is myocardial infarction.

Certain embodiments of the invention provide the use of a nanoparticle or compound as described herein to prepare a medicament useful for treating a pathological fibrin associated disorder in an animal.

Certain embodiments of the invention provide a nanoparticle or compound as described herein for use in therapy.

Certain embodiments of the invention provide a nanoparticle or compound as described herein for prophylactic or therapeutic use in treating a pathological fibrin associated disorder.

Certain embodiments of the invention provide a nanoparticle or compound as described herein for use in medical treatment or diagnosis.

BRIEF DESCRIPTION OF THE FIGURES

FIG. 2A. Illustration of coagulation cascade. FIG. 2B. Illustration of streptokinase mechanism of action.

FIG. 5A. Illustration of the experimental design of the cell uptake assay. The circles represent the nanoparticles loaded with coumarin-6; A549 cells were seeded in the lower chamber and the upper chamber contained gelled bovine fibrinogen, human thrombin and sodium chloride. FIG. 5B. Illustration of cell uptake study results for with fibrin gel (left) and without fibrin gel (right) using blank NP (1), SK NP (2) and blank NP+SK (3).

FIG. 6A. Illustration of the experimental design for the rate of migration through fibrin gels. The circles represent the SK nanoparticles loaded with paclitaxel. A gelled solution of bovine fibrinogen, human thrombin and sodium chloride was added to the inserts of a 12-well Transwell plate. Nanoparticles were added to the upper chamber. The lower chamber contained 1 mL distilled water. FIG. 6B. Graphical illustration of the rate of migration through fibrin gels: cumulative amount of nanoparticle (ng) versus time (hours). Plasminogen (−) fibrin gel is shown by circles and plasminogen (+) fibrin gel is shown by squares.

FIGS. 8A-C. Cell uptake study. Nanoparticles loaded with a fluorescent dye (coumarin-6) were added to A549 cells directly or separated from them by fibrin gels. After 24 hours, cells were collected and washed to remove surface bound NPs. The cells were then analyzed using flow cytometry. (FIG. 8A) There is significant reduction in the cellular uptake of blank nanoparticles when they are separated from the cells by fibrin gels. (FIG. 8B) SK NPs show comparable cellular uptake even in the presence of fibrin gels. (FIG. 8C) Positive control i.e. blank nanoparticles with free SK shows results similar to (FIG. 8B).

FIGS. 9A-B. Intratumoral distribution of nanoparticles. Nanoparticles with (treatment) (FIG. 9A) or without (control) (FIG. 9B) human plasminogen incubation were injected intratumorally at a rate of 0.1 mcL/min over 10 minutes. The animals were imaged using Xenogen IVIS live animal imaging. Control nanoparticles show very limited distribution within the tumor (FIG. 9A), while nanoparticles incubated with plasminogen show significant distribution (FIG. 9B).

DETAILED DESCRIPTION

Figure 1:
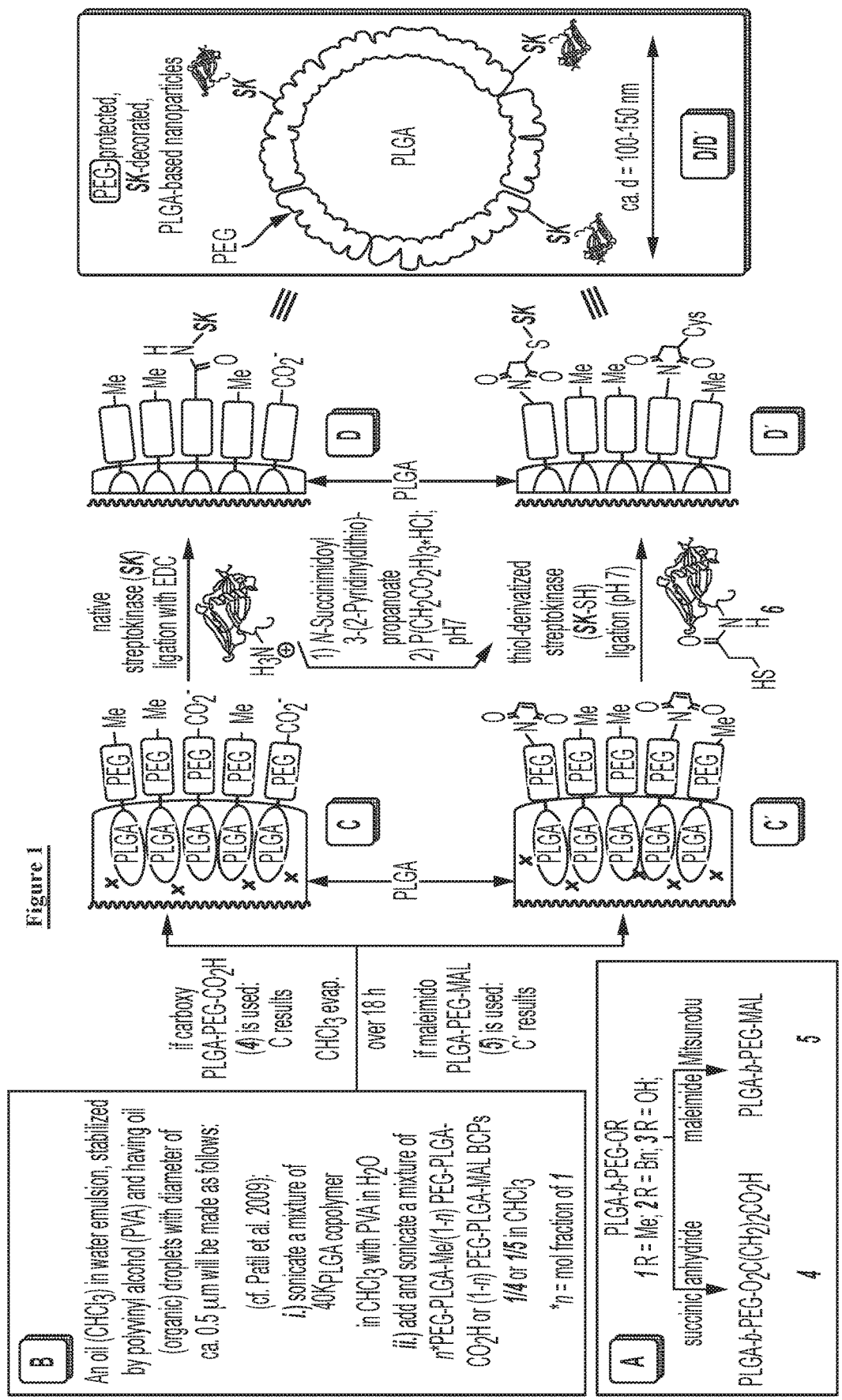
FIG. 1. Methods for synthesis of BCPs 1, 4, and 5 and their use in preparation of SK-decorated NPs D/D'.

Certain embodiments of the invention provide a nanoparticle covalently attached directly or indirectly through a linker to one or more moieties independently selected from streptokinase (kabinkinase, streptase), urokinase (abbokinase), arvin, brinase, tissue plasminogen activator (tPA), recombinant tissue plasminogen activator (r-tPA), nattokinase, lumbrokinase, serrapeptase, prourokinase, reptilase, anisoylated purified streptokinase activator complex (APSAC), thrombinase, anistreplase (eminase) and staphylokinase. In certain embodiments the recombinant tissue plasminogen activator is reteplase (retavase), alteplase (activase), tenecteplase (TNKase) or lanoteplase.

In certain embodiments, the one or more moieties are independently selected from urokinase, staphylokinase, alteplase, reteplase, tenecteplase and lanoteplase.

In certain embodiments, the one or more moieties are streptokinase.

As described herein, thrombolytic (thrombus or clot-splitting) or fibrinolytic (fibrin splitting) therapeutics may be used, including, for example, streptokinase (i.e., Kabikinase, Streptase; thrombolytic enzyme derived from bacteria), urokinase (Abbokinase; thrombolytic derived from human urine), arvin (thrombolytic derived from a Malayan pit viper), brinase (thrombolytic derived from the mold *Asperfillus oryzae*), retavase (i.e., reteplase; thrombolytic; recombinant tissue plasminogen activator (r-tPA)), tissue plasminogen activator (tPA; thrombolytic), activase (i.e., alteplase; thrombolytic prototype; recombinant tissue plasminogen activator (r-tPA)), tenecteplase (TNKase; thrombolytic; recombinant tissue plasminogen activator (r-tPA)), anistreplase (Eminase; thrombolytic), Nattokinase (derived from fermented soy and the bacteria *Bacillus natto*), Lumbrokinase (i.e., earthworm powder), Serrapeptase (i.e., *Serratia* peptidase; a proteolytic enzyme isolated from the non-pathogenic enterobacteria *Serratia* E15), prourokinase, reptilase, anisoylated purified streptokinase activator complex (APSAC), and thrombinase (derived from cultures of *Bacillus sphaericus*).

In certain embodiments of the invention, the nanoparticle covalently attached directly or indirectly through a linker to one or more moieties has a diameter of about 3 nm to about 1,000 nm. In certain embodiments, the nanoparticle has a diameter of about 3 nm to about 10 nm. In certain embodiments, the nanoparticle has a diameter of about 10 nm to about 1000 nm. In certain embodiments, the nanoparticle has a diameter of about 50 nm to about 1000 nm. In certain embodiments, the nanoparticle has a diameter of about 50 nm to about 500 nm. In certain embodiments, the nanoparticle has a diameter of about 50 nm to about 300 nm. In certain embodiments, the nanoparticle has a diameter of about 100 nm to about 300 nm. In certain embodiments, the nanoparticle has a diameter of about 150 nm to about 300 nm. In certain embodiments, the nanoparticle has a diameter of about 200 nm to about 250 nm. In certain embodiments, the nanoparticle has a diameter of about 100 nm to about 200 nm. In certain embodiments of the invention, the nanoparticle has a diameter of about 100 nm to about 150 nm.

In certain embodiments of the invention, the diameter is measured using dynamic light scattering (DLS).

In certain embodiments, the nanoparticle comprises poly-(lactic-co-glycolic acid).

In certain embodiments of the invention, the nanoparticle comprises a dendrimer, a quantum dot, a metal, a metal-oxide, a polymer, a polymer conjugate (e.g., a polymer conjugated to a drug or an antibody) or a polymer-macromolecular complex (e.g., a cationic polymer complexed with an anionic macromolecule, such as a nucleic acid).

In certain embodiments, the polymer is selected from poly-(lactic-co-glycolic acid), polyanhydride, polysulfonamide, alginate, chitosan, polyethyleneimine, polyethylene glycol, poly-L-lysisne, polyglutamic acid, cellulosic derivatives (e.g., ethyl cellulose), and acrylic acid based polymers (e.g., hydroxypropyl methacrylamide). In certain embodiments, the polymer is poly-(lactic-co-glycolic acid). In certain embodiments, the poly-(lactic-co-glycolic acid) has an average molecular weight of about 15,000 daltons to about 150,000 daltons. In certain embodiments, the poly-(lactic-co-glycolic acid) has an average molecular weight of about 30,000 daltons to about 50,000 daltons. In certain embodiments, the poly-(lactic-co-glycolic acid) has an average molecular weight of about 40,000 daltons.

In certain embodiments, the metal is selected from gold, iron, silver and gadollinium.

In certain embodiments, the nanoparticle further comprises one or more targeting ligands covalently attached to the nanoparticle directly or indirectly through a linker. In certain embodiments, the targeting ligand associates with a tumor cell. In certain embodiments, the targeting ligand binds to a tumor cell. In certain embodiments, the targeting ligand is independently selected from folic acid, biotin, a Cys-Arg-Glu-Lys-Ala (CREKA) peptide, transferrin, a peptide targeting transferrin receptor, an epidermal growth factor receptor (EGFR) targeting peptide, a single chain variable fragment (scFv) or antibody, a CD133 targeting scFv or antibody, and a peptide targeting the integrin receptors.

In certain embodiments of the invention, the linker does not interfere with the activity of the one or more moieties or the one or more targeting ligands.

In certain embodiments, the linker comprises poly-(ethylene glycol) or poly-(ethylene oxide).

In certain embodiments, the linker comprises poly-(ethylene glycol). In certain embodiments, the poly-(ethylene glycol) has an average molecular weight of about 2,000 daltons to about 20,000 daltons. In certain embodiments, the average molecular weight is about 5,000 daltons.

In certain embodiments, the linker comprises poly-(ethylene oxide). In certain embodiments, the poly-(ethylene oxide) has an average molecular weight of about 2,000 daltons to about 20,000 daltons. In certain embodiments, the average molecular weight is about 5,000 daltons.

In certain embodiments, the linker comprises a functionalized terminal moiety. As used herein, the phrase "functionalized terminal moiety" is a group that is capable of attaching to something further (e.g., capable of attaching to one or more moieties or one or more targeting ligands). In certain embodiments, the functionalized terminal moiety is carboxy, maleimide, sulfhydryl, aldehyde, azide or amino. In certain embodiments, the functionalized terminal moiety is carboxy. In certain embodiments, the functionalized terminal moiety is maleimide.

In certain embodiments, the linker comprises a block co-polymer selected from poly-lactic acid and poly-(ethylene glycol); poly-lactic acid and poly-(ethylene oxide); poly-(lactic-co-glycolic acid) and poly-(ethylene glycol); and poly-(lactic-co-glycolic acid) and poly-(ethylene oxide).

In certain embodiments, the poly-(ethylene glycol) or the poly-(ethylene oxide) comprises a functionalized terminal moiety. In certain embodiments, the moiety is carboxy, maleimide, sulfhydryl, aldehyde, azide or amino. In certain embodiments, the moiety is carboxy. In certain embodiments, the moiety is maleimide.

In certain embodiments, the block co-polymer is poly-lactic acid and poly-(ethylene glycol). In certain embodiments, the poly-lactic acid has an average molecular weight of about 3,000 daltons to about 8,000 daltons. In certain embodiments, the poly-(ethylene glycol) has an average molecular weight of about 2,000 daltons to about 20,000 daltons. In certain embodiments, the poly-(ethylene glycol) has an average molecular weight of about 5,000 daltons. In certain embodiments, the block co-polymer is poly-(lactic-co-glycolic acid) and poly-(ethylene glycol). In certain embodiments, the poly-(lactic-co-glycolic acid) has an average molecular weight of about 3,000 daltons to about 8,000 daltons. In certain embodiments, the poly-(ethylene glycol) has an average molecular weight of about 2,000 daltons to about 20,000 daltons. In certain embodiments, the poly-(ethylene glycol) has an average molecular weight of about 5,000 daltons.

In certain embodiments, the poly-(ethylene glycol) comprises a functionalized terminal moiety. In certain embodiments, the moiety is carboxy, maleimide, sulfhydryl, aldehyde, azide or amino. In certain embodiments, the moiety is carboxy. In certain embodiments, the moiety is maleimide.

In certain embodiments, the block co-polymer is poly-lactic acid and poly-(ethylene oxide). In certain embodiments, the poly-lactic acid has an average molecular weight of about 3,000 daltons to about 8,000 daltons. In certain embodiments, the poly-(ethylene oxide) has an average molecular weight of about 2,000 daltons to about 20,000 daltons. In certain embodiments, the poly-(ethylene oxide) has an average molecular weight of about 5,000 daltons. In certain embodiments, the block co-polymer is poly-(lactic-co-glycolic acid) and poly-(ethylene oxide). In certain embodiments, the poly-(lactic-co-glycolic acid) has an average molecular weight of about 3,000 daltons to about 8,000 daltons. In certain embodiments, the poly-(ethylene oxide) has an average molecular weight of about 2,000 daltons to about 20,000 daltons. In certain embodiments, the poly-(ethylene oxide) has an average molecular weight of about 5,000 daltons.

In certain embodiments, the poly-(ethylene oxide) comprises a functionalized terminal moiety. In certain embodiments, the functionalized terminal moiety is carboxy, maleimide, sulfhydryl, aldehyde, azide or amino. In certain embodiments, the functionalized terminal moiety is carboxy. In certain embodiments, the functionalized terminal moiety is maleimide.

In certain embodiments of the invention, the nanoparticle further comprises one or more therapeutic agents. In certain embodiments, the one or more therapeutic agents may be associated with the nanoparticle. For example, when the nanoparticle comprises a polymer, the one or more therapeutic agents may be conjugated to the polymer or dispersed in the polymer matrix.

In certain embodiments, the one or more therapeutic agents is an anti-cancer agent. As used herein, the phrase "anti-cancer agent" can refer to an agent that inhibits the proliferation, growth, life-span or metastatic activity cancer cells. In certain embodiments, the anti-cancer agent is independently selected from All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, tyrosine kinase inhibitors, an antibody (e.g., Herceptin and bevacizumab), and pharmaceutically acceptable salts thereof, or combinations thereof. In certain embodiments, the tyrosine kinase inhibitors are Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib or Vandetanib. In certain embodiments, the anti-cancer agent is Paclitaxel. In certain embodiments, the anti-cancer agent is a silicate prodrug of Paclitaxel.

In certain embodiments, of the invention, the nanoparticle further comprises one or more bioactive agents. In certain embodiments, the one or more bioactive agents may be associated with the nanoparticle. For example, when the nanoparticle comprises a polymer, the one or more bioactive agents may be conjugated to the polymer or dispersed in the polymer matrix. In certain embodiments, the one or more bioactive agents are independently selected from a small molecule, a protein and a nucleic acid.

In certain embodiments of the invention, the nanoparticle further comprises one or more imaging agents. In certain embodiments, the one or more imaging agents may be associated with the nanoparticle. For example, when the nanoparticle comprises a polymer, the one or more imaging agents may be conjugated to the polymer or dispersed in the polymer matrix. In certain embodiments of the invention, the nanoparticle further comprises one or more imaging agents independently selected from coumarin-6, SDB5491, rhodamine derivatives, cy5.5, radiolabels for PET imaging and diagnostic agents suitable for MRI imaging (e.g. gadolinium). In certain embodiments, the imaging agent is coumarin-6. In certain embodiments, the imaging agent is SDB5491.

Certain embodiments of the invention provide, a compound of formula (I):

A-B-C-D        (I)

wherein A is poly-lactic acid or and poly-(lactic-co-glycolic acid); B is poly-(ethylene glycol) or poly-(ethylene oxide); C is methyl and D is absent; or C is a linking group and D is one or more moieties independently selected from streptokinase (kabinkinase, streptase), urokinase (abbokinase), arvin, brinase, tissue plasminogen activator (tPA), recombinant tissue plasminogen activator (r-tPA), nattokinase, lumbrokinase, serrapeptase, prourokinase, reptilase, anisoylated purified streptokinase activator complex (APSAC), thrombinase, anistreplase (eminase) and staphylokinase.

In certain embodiments, A is poly-lactic acid. In certain embodiments, A is poly-(lactic-co-glycolic acid). In certain embodiments, the average molecular weight of A is about 3,000 daltons to about 8,000 daltons.

In certain embodiments, B is poly-(ethylene glycol). In certain embodiments, B is poly-(ethylene oxide). In certain embodiments, the average molecular weight of B is about 2,000 daltons to about 20,000 daltons. In certain embodiments, the average molecular weight of B is about 2,000 daltons to about 10,000 daltons. In certain embodiments, the average molecular weight of B is about 5,000 daltons.

In certain embodiments, the linking group does not interfere with the activity of D. In certain embodiments, the linking group is a direct bond, carboxy, —OC(=O)(CH$_2$)$_n$C(=O)O—, maleimide, sulfhydryl, aldehyde, azide, or amino, wherein n is 1-10. In certain embodiments, the linking group is carboxy. In certain embodiments, the linking group is maleimide.

In certain embodiments, C is methyl and D is absent.

In certain embodiments, C is a linking group and D is one or more moieties independently selected from streptokinase (kabinkinase, streptase), urokinase (abbokinase), arvin, brinase, tissue plasminogen activator (tPA), recombinant tissue plasminogen activator (r-tPA), nattokinase, lumbrokinase, serrapeptase, prourokinase, reptilase, anisoylated purified streptokinase activator complex (APSAC), thrombinase, anistreplase (eminase) and staphylokinase.

In certain embodiments, the recombinant tissue plasminogen activator is reteplase (retavase), alteplase (activase), tenecteplase (TNKase) or lanoteplase.

In certain embodiments, D is independently selected from urokinase, staphylokinase, alteplase, reteplase, tenecteplase and lanoteplase.

In certain embodiments, D is streptokinase.

Certain embodiments of the invention provide a nanoparticle comprising poly-(lactic-co-glycolic acid) and one or more units of formula (I) as described herein.

In certain embodiments, the average molecular weight of the poly-(lactic-co-glycolic acid) is about 15,000 daltons to about 150,000 daltons. In certain embodiments, the poly-(lactic-co-glycolic acid) has an average molecular weight of about 30,000 daltons to about 50,000 daltons. In certain embodiments, the average molecular weight of the poly-(lactic-co-glycolic acid) is about 40,000 daltons.

In certain embodiments, the one or more units of formula (I) are associated with the poly-(lactic-co-glycolic acid).

In certain embodiments, the one or more units of formula (I) are associated with the poly-(lactic-co-glycolic acid) through A. In certain embodiments, A is embedded or partially embedded in the poly-(lactic-co-glycolic acid).

In certain embodiments, the nanoparticle comprises a plurality of compounds of formula (I). In certain embodiments, the compounds of formula (I) may be the same or different. In certain embodiments, the compounds of formula (I) are the same. In certain embodiments, the compounds of formula (I) are different.

In certain embodiments, the nanoparticle has a diameter of about 50 nm to about 1000 nm. In certain embodiments, the nanoparticle has a diameter of about 50 nm to about 500 nm. In certain embodiments, the nanoparticle has a diameter of about 50 nm to about 300 nm. In certain embodiments, the nanoparticle has a diameter of about 100 nm to about 300 nm. In certain embodiments, the nanoparticle has a diameter of about 150 nm to about 300 nm. In certain embodiments, the nanoparticle has a diameter of about 200 nm to about 250 nm. In certain embodiments, the nanoparticle has a diameter of about 100 nm to about 200 nm. In certain embodiments, the nanoparticle has a diameter of about 100 nm to about 150 nm.

In certain embodiments of the invention, the nanoparticle further comprises one or more therapeutic agents. In certain embodiments, the one or more therapeutic agents may be dispersed in the matrix of the poly-(lactic-co-glycolic acid). In certain embodiments, the one or more therapeutic agents is an anti-cancer agent. As used herein, the phrase "anti-cancer agent" can refer to an agent that inhibits the proliferation, growth, life-span or metastatic activity of cancer cells. In certain embodiments, the anti-cancer agent is independently selected from All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, tyrosine kinase inhibitors, an antibody (e.g., Herceptin and bevacizumab), and pharmaceutically acceptable salts thereof, or combinations thereof. In certain embodiments, the tyrosine kinase inhibitors are Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib or Vandetanib. In certain embodiments, the anti-cancer agent is Paclitaxel. In certain embodiments, the anti-cancer agent is a silicate prodrug of Paclitaxel.

In certain embodiments, of the invention, the nanoparticle further comprises one or more bioactive agents. In certain embodiments, the one or more bioactive agents may be dispersed in the matrix of the poly-(lactic-co-glycolic acid). In certain embodiments, the one or more bioactive agents are a small molecule, a protein or a nucleic acid.

In certain embodiments of the invention, the nanoparticle further comprises one or more imaging agents. In certain embodiments, the one or more imaging agents are dispersed in the matrix of the poly-(lactic-co-glycolic acid). In certain embodiments of the invention, the nanoparticle further comprises one or more imaging agents independently selected from coumarin-6, SDB5491, rhodamine derivatives, cy5.5, radiolabels for PET imaging and diagnostic agents suitable for MRI imaging (e.g. gadolinium). In certain embodiments, the imaging agent is coumarin-6. In certain embodiments, the imaging agent is SDB5491.

Certain embodiments of the invention provide compound or nanoparticle as described herein.

Certain embodiments of the invention provide a pharmaceutical composition comprising a nanoparticle or compound as described herein and a pharmaceutically acceptable carrier.

Certain embodiments of the invention provide a method of delivering a therapeutic agent and/or an imaging agent to a cell, comprising contacting the cell with a nanoparticle as described herein. In certain embodiments, the contacting occurs in vitro. In certain embodiments the contacting occurs in vivo. In certain embodiments, the nanoparticle described herein is incubated with plasminogen prior to contacting. In certain embodiments, the plasminogen is human plasminogen.

Certain embodiments of the invention provide a method of dissolving fibrin in a sample (e.g., a sample comprising cells, such as cancer cells) comprising contacting the sample with a nanoparticle or compound as described herein. In certain embodiments, the nanoparticle or compound described herein is incubated with plasminogen prior to contacting. In certain embodiments, the plasminogen is human plasminogen.

Certain embodiments of the invention provide a method of delivering a therapeutic agent to an animal (e.g., a human) in need thereof, comprising administering to the animal a nanoparticle as described herein.

Certain embodiments of the invention provide a method of delivering an imaging agent to an animal (e.g., a human) in need thereof, comprising administering to the animal a nanoparticle as described herein.

Certain embodiments of the invention provide a method for treating a pathological fibrin associated disorder in an animal (e.g., a human), comprising administering to the animal a nanoparticle or compound as described herein.

In certain embodiments, the nanoparticle or compound described herein is incubated with plasminogen prior to administration. In certain embodiments, the plasminogen is human plasminogen.

In certain embodiments, the pathological fibrin associated disorder is cancer. In certain embodiments, the cancer is lung cancer, pancreatic cancer or breast cancer. In certain embodiments, the cancer is a metastatic outgrowth.

In certain embodiments, the pathological fibrin associated disorder is myocardial infarction.

Certain embodiments of the invention provide the use of a nanoparticle or compound as described herein to prepare a medicament useful for treating a pathological fibrin associated disorder in an animal (e.g., a human).

Certain embodiments of the invention provide a nanoparticle or compound as described herein for use in therapy.

Certain embodiments of the invention provide a nanoparticle or compound as described herein for prophylactic or therapeutic use in treating a pathological fibrin associated disorder.

Certain embodiments of the invention provide a nanoparticle or compound as described herein for use in medical treatment or diagnosis.

Certain embodiments of the invention also provide processes and intermediates disclosed herein that are useful for preparing nanoparticles or compounds described herein.

As used herein, the terms "treat" and "treatment" can refer to therapeutic treatment and prophylactic or preventative treatment. In some embodiments of the invention, the object is to prevent or decrease the development of cancer.

The term "peptide" describes a sequence of 2 to 25 amino acids (e.g. as defined hereinabove) or peptidyl residues.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The present nanoparticles and compounds of formula I can be formulated as pharmaceutical compositions and administered to a mammalian host, such as a human patient in a variety of forms adapted to the chosen route of administration, i.e., parenterally, by intravenous, intramuscular, topical or subcutaneous routes.

Thus, the present nanoparticles and compounds may be systemically administered, in combination with a pharmaceutically acceptable vehicle such as an inert diluent or a carrier. In addition, the active compound (i.e., the nanoparticles and compounds described herein) may be incorporated into sustained-release preparations and devices.

The active compound may also be administered intravenously or intraperitoneally by infusion or injection. Dispersions of the present nanoparticles or compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present nanoparticles and compounds may be applied in pure form, i.e., when they are liquids. However, it will generally be desirable to administer them to the skin as compositions or formulations, in combination with a dermatologically acceptable carrier, which may be a solid or a liquid. In addition, the active may be delivered into the skin through the use of devices such as microneedles or needle-less injections.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the present nanoparticles or compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the present nanoparticles or compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the present nanoparticle or compound, required for use in treatment will vary with the route of administration, the nature of the condition being treated and the age and condition of the patient and will be ultimately at the discretion of the attendant physician or clinician.

The nanoparticles and compounds of the present invention can be conveniently formulated in unit dosage form. In one embodiment, the invention provides a composition comprising the nanoparticles or compounds of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

Example 1

Inefficient transport of drug delivery systems through tumor extracellular matrix (ECM) severely limits therapeutic efficacy. Tumors are characterized by the presence of a neo-vasculature that is underdeveloped and leaky. This leads to deposition of fibrin, a key ingredient of blood clot, within the tumor matrix (M. Schafer, S. Werner, *Nat Rev Mol Cell Biol* 9, 628 (2008)). The presence of fibrin is an important cause of elevated interstitial fluid pressure (IFP) in tumors (J. Ma, D. J. Waxman, *Mol Cancer Ther* 7, 3670 (2008)). Elevated IFP, in turn, results in increased resistance to convective transport of drug carriers in the tumor matrix and decreases the amount of drug reaching tumor cells (L. T. Baxter, R. K. Jain, *Microvasc Res* 37, 77 (1989)). This is especially true for central regions of the tumor, which are typically under-perfused. This is a critical problem because these poorly-perfused regions (which have low pH and low $pO_2$) harbor the most aggressive and drug-resistant tumor cells.

Drug-loaded polymeric nanoparticles (NPs) with improved tumor penetration and intra-tumoral distribution are described below. These NPs may be surface functionalized with the bacterial enzyme streptokinase (SK). This enzyme activates human plasminogen to plasmin and triggers lysis of the fibrin clot (N. Alkjaersig, et al., *J Clin Invest* 38, 1086 (1959)) and has previously been used as a clot-dissolving agent for treatment of some heart attack or pulmonary embolism victims. SK-functionalized NPs may be loaded with a drug or imaging agent. For examples, the NPs may be used as a carrier for the delivery of anticancer therapeutics (e.g. to treat tumors that have an abundance of/overexpress fibrin in the ECM, such as, for example, lung, pancreatic or breast tumors).

The development of poly(lactic-co-glycolic acid) (PLGA, a polymer acceptable to the FDA) NPs that are surface-functionalized with SK are described herein. A novel surface-functionalization technology that enables the incorporation of stabilizing polyethylene glycol (PEG) polymers and other molecules on the surface of drug-loaded NPs without significant loss of the drug payload has been developed (Y. B. Patil, et al., *Biomaterials* 30, 859 (2009)). This technology may be used to incorporate SK onto the surface of similar NPs, which will improve their tumor penetration, literally by chewing their way through the ECM.

The design and development of SK-functionalized NPs that are optimized for maximal intra-tumoral distribution are described herein. In vitro studies that will demonstrate the ability of SK-functionalized NPs to penetrate and distribute through fibrin-based hydrogels that mimic tumor ECM are also described. Accordingly, the following studies may be performed:

Fabrication of SK-Functionalized Nanoparticles:

An array of NPs having the general form depicted as D/D' in FIG. 1 will be synthesized. These are based on a hydrophobic PLGA core that can be loaded with various bioactive agents (cf. χ in C or C'). These particles are also capable of being produced in size regimes that permit passive localization at solid tumors via the EPR effect. The particles are stabilized by an exterior of amphiphilic PLGA-PEG (5K-5K) block copolymers (ovals-rounded rectangles in FIG. 1). These create a watery PEG corona that allows the NPs to be formulated as stable dispersions in physiologic fluids. Importantly, the particle surfaces can be decorated with different surface densities of SK.

A strategy for synthesis of drug-loaded NPs displaying biotin on their surface using an oil ($CHCl_3$, PLGA) in water emulsion (PVA) technique (cf. box B in FIG. 1) has been developed (Y. Patil, T. Sadhukha, L. Ma, J. Panyam, *J Control Release* 136, 21 (2009)), and a similar protocol may be used herein. Particle formation is achieved by slow evaporation of $CHCl_3$ from an emulsion made as described in box B. These NPs (d=100-150 nm) are then pelletized (centrifugation), washed, and lyophilized. The isolated powder is resuspended in suitable buffer for use in subsequent studies.

The requisite PLGA-b-PEG copolymers 4 and 5 (box A, FIG. 1) will be synthesized in order to ligate SK onto the NP surface. Methods have been developed for the synthesis of polymers 1 and 3. These polymers are also available commercially. To produce 4 or 5, the terminal primary alcohol in 3 will be succinoylated or displaced with maleimide (MAL, diethyl azodicarboxylate, $Ph_3P$). SK itself, which contains a number of its 29 lysines on its surface, will be coupled to surface carboxylic acids in C using 1-ethyl-3-(3-dimethylaminopropyl) carbodiimide (EDC). As an alternative strategy for surface ligation, SK (which contains no cysteine or cystine residues) may be lightly derivatized with a mercaptan appendage (cf. 6) and that thiol may be coupled to a portion of the MALs in C'. The remaining MALs will be capped by addition of excess cysteine to provide D'.

Characterization of Nanoparticles.

A number of chemical tests will be performed, most ultimately relying on NMR spectroscopic analysis, to analyze the composition of these particle preparations at various stages. For example, lyophilized samples of particles C/C'/D/D' can be disassembled by dissolution in $CDCl_3$ and then analyzed by $^1H$ NMR spectroscopy (U. S. Toti, et al., *Mol Pharm* 7, 1108 (2010)). Also, particle samples C or C' will be exhaustively ligated with an excess of the small amine p-MeOPhCH$_2$NH$_2$ or thiol 4-MePhSH and then NMR analysis (including PEG end-groups (S. Ji, et al., *Macromol Chem Phys* 210, 823 (2009)) will be carried out to determine the number of addressable surface acids or maleimides, respectively. Particle size and surface charge (zeta potential) will be measured using dynamic light scattering (DLS). Various electron microscopy experiments will be performed to validate the information gained from DLS measurements. Particle stability will be monitored by DLS over time as well as prior to and following lyophilization and redispersion in buffer. The total amount of SK protein present in the final particle preparation will be determined by standard protein measurement techniques such as the Bradford assay. Finally, the peptidase activity of the loaded SK will be assessed by using commercially available substrate that is cleaved to produce a colored product. Both density of SK loading and method of ligation will be correlated with activity. This information may be used to assess and select NPs for drug-loading.

Diffusion of Particles Through Fibrin Gels:

Fibrin gels will be cast in situ in microslide capillary tubes by dispersing thrombin and plasminogen in a fibrinogen solution and incubating the system at 37° C. for a few minutes. Following the introduction of NPs on one end of the gel, diffusion of the particles across the gel will be characterized by measuring the fluorescence intensity as a function of distance and time in the gel using a laser scanning microscope. Relative diffusion coefficients of NPs loaded with different concentrations of SK will help determine optimum SK concentration for future studies. Diffusion coefficients will be calculated using the relationship in eq. (1) below (C. Wong et al., *Proc Natl Acad Sci USA* 108, 2426 (2011)), where $\chi$ is the distance from one end of the tube, t is the time of measurement, C is the fluorescence intensity, and D is the diffusion coefficient.

$$C(\chi, t) \alpha \operatorname{erfc}\left\{\frac{\chi}{2 \cdot \sqrt{D \cdot t}}\right\} \quad \text{eq. (1)}$$

Cell Uptake Studies:

Cell uptake of eventual drug-loaded NPs is of therapeutic advantage. To determine optimum SK loading levels compatible with this important property, uptake of NPs D/D' will be performed in vitro. A549 lung cancer cells and PC3 prostate cancer cells will be used because these cancers are associated with high fibrin content. Fibrin gels will be formed in the upper chamber of trans-well plates while the lower chamber will be seeded with cells. Diffusion of the particles through the fibrin gel and uptake by the cells will be measured for 6-coumarin loaded particles using flow cytometry. Non-functionalized particles will be used as a negative control.

Example 2

Distribution of nutrients and drugs in most organs is governed by convective flow of blood to the organ and diffusion of the molecule in the organ. In solid tumors, this distribution is dictated by the tumor microenvironment and is highly irregular leading to regions lacking oxygen (hypoxia) and essential nutrients. These regions harbor cells that are most virulent and often responsible for tumor relapse and resistance; adequate drug levels are needed in these regions for complete remission.

Factors that affect intratumoral distribution include the tumor microenvironment (e.g., vascular architecture, ECM and IFP) and the physicochemical properties of drugs (e.g., size and charge). The rate of tumor cell growth is greater than the rate at which blood capillary cells proliferate. Accordingly, pro-angiogenic factors are not secreted uniformly throughout the tumor, which leads to abnormal vasculature that does not span the complete tumor volume. Additionally, the distribution of macromolecules and drug carriers like nanoparticles in a tumor is severely affected by the deposition of vascular proteins. Blood vessels supplying tumors are often leaky, which leads to expulsion of vascular proteins in the extracellular spaces. Hence, the ECM in tumors is extremely dense and tortuous; the ECM is characterized by the presence of fibrous material (e.g., collagen, elastin and fibrin), proteoglycans (e.g., glycosaminoglycans, and condroitin) and nonproteoglycans (e.g. hyaluronic acid). The presence of ECM proteins and increasing number of cells compresses the blood vessels. As convective flow in the blood vessels diminishes, diffusion is the only mode of transport for the drug in the tumor microenvironment. Tortuosity in the ECM, therefore, plays a major role impeding the movement of the drug in the tumor matrix. Since diffusion is the major determinant of the distribution of the drug in the tumor matrix, size is of primary importance (the diffusion coefficient (D) may be calculated using the Stokes Einstein equation ($D=(k_BT)/(6\pi r\eta)$), wherein r is radius)). Drug charge also plays a role in movement: the endothetial surface bears a net negative charge, and therefore, negatively charged molecules experience significant resistance to extravasation and distribution.

Various strategies have been previously used to improve tumor distribution by targeting the certain components of the ECM (Diop-Frimpong et al., P.N.A.S., U.S.A., 108(7): 2909-12 (2011); Guedan, et al., Mol. Ther., 18(7): 1275-83 (2010); Eikenes, et al., Cancer Res. 64(14): 4768-73 (2004); and Kato et al., Int. J. Pharm., in press (December 2011)). For example, previous reports have utilized protein degrading enzymes such as collagenase to improve the penetration of drugs and macromolecules. However, the substrate for this enzyme, collagen, is present in a number of normal tissues. The ubiquitous existence of these targeted ECM components leads to their non-specific degradation and excess loss of ECM in the tumor leads to increased events of metastasis. Hence, collagenase and other proteases in general cannot be used in the clinic.

Figure 2A:
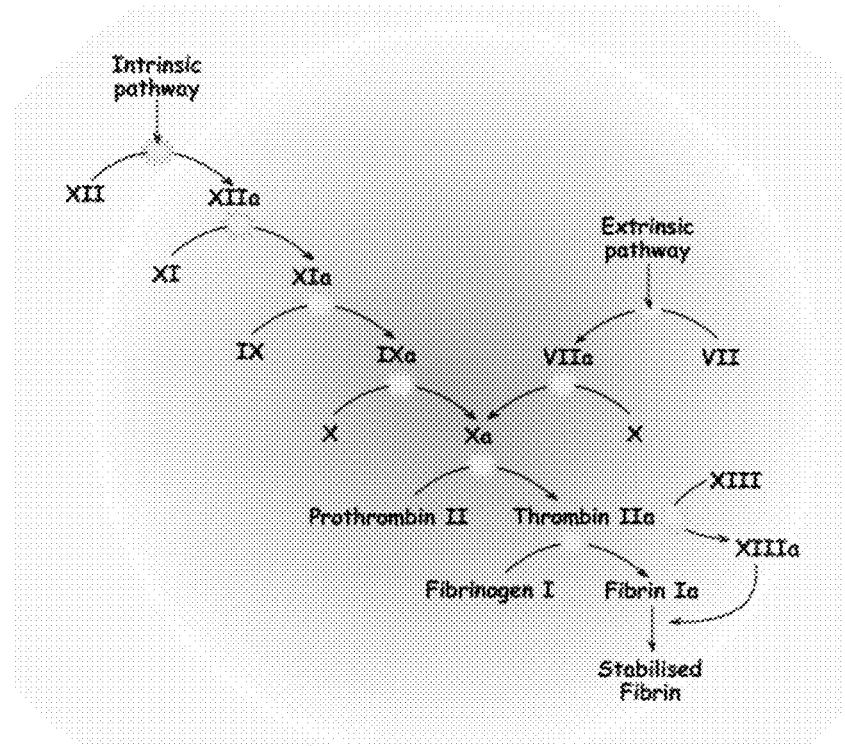
FIGS. 2A-B.

Alternatively, as described herein, fibrin may be targeted as a strategy to improve tumor distribution: the presence of fibrin in the ECM contributes to inefficient distribution of drugs in a tumor and degradation of the fibrin meshwork in tumors should allow uniform intra-tumoral distribution of the drug and hence better therapeutic efficacy. Fibrin is the key ingredient of a blood clot and plays a major role in wound healing (FIG. 2A). It exists in blood as a soluble protein fibrinogen. Tumors and wounds have several characteristics in common, such as leaky blood vessels, angiogenesis, migration of inflammatory cells and fibrin deposition; however, the inactivation of coagulation factors occurs in wounds but not tumors. In the absence of wounding, fibrin would only exist in the tumor matrix. Accordingly, off-target effects could be avoided.

Figure 2B:
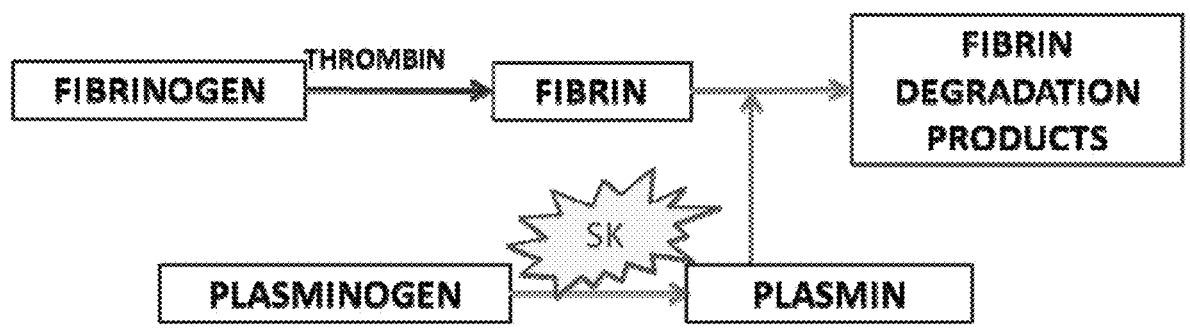
Figure 3:
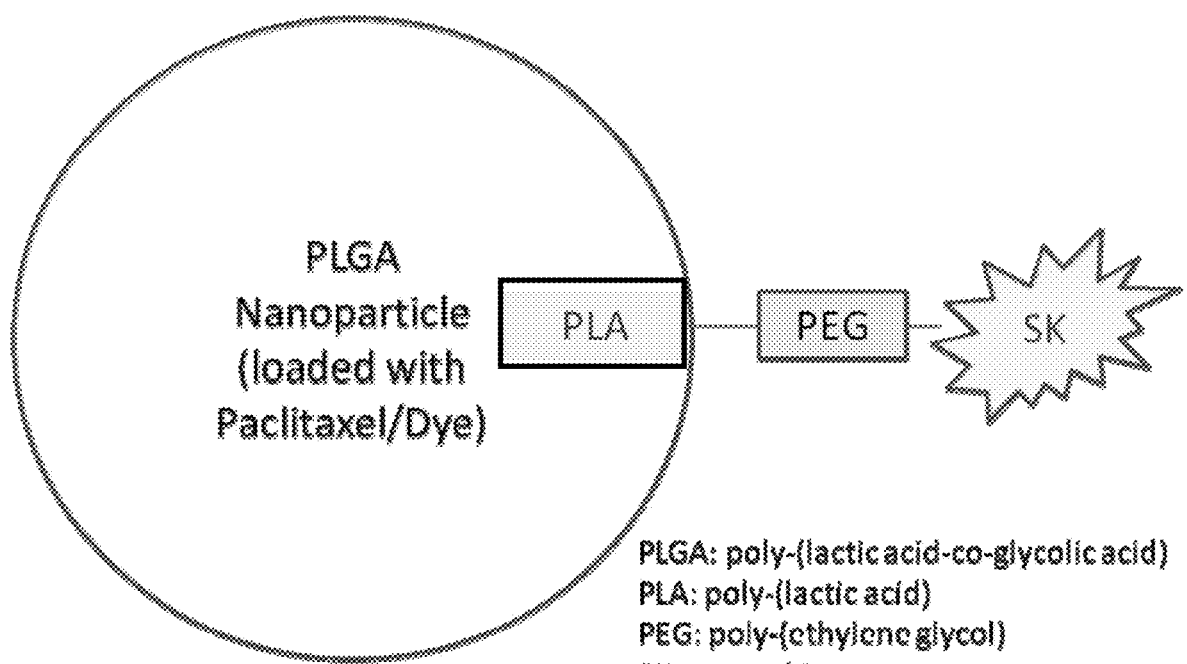
FIG. 3. Illustration of a nanoparticle design.

As described herein, to aid the movement of nanoparticles in this dense tumor microenvironment, nanoparticles were functionalized with the enzyme Streptokinase. Streptokinase is a fibrinolytic enzyme isolated from bacterial origin (FIG. 2B) and is very specific to fibrin. Streptokinase has been previously used in the clinic to dissolve harmful blood clots (e.g., in the brain, myocardial infarction or pulmonary embolism). Specifically, the enzyme is covalently attached to the surface of nanoparticles to improve its penetration. In contrast to previous attempts to simply co-inject collagenase with macromolecules directly into the tumor, these functionalized nanoparticles can be injected into the blood without any potential side effects. Accordingly, streptokinase dissolves the fibrin/fibrin network in the tumor and enables the nanoparticles to migrate through the ECM more efficiently and is hence capable of improving the distribution of nanoparticles within tumors (e.g., nanoparticles with encapsulated therapeutic agents, such as paclitaxel and other anti-cancer agents (see FIG. 3)).

Previously developed nanoparticulate systems extravasate into the tumor by the enhanced permeability and retention (EPR) effect. However due to the lack of convective flow, the distribution of these systems heavily relies on their diffusion in the tumor matrix. Owing to their size and the dense nature of the tumor matrix, this is strongly impeded. This leads to insufficient amount of drug reaching the core of the tumor and hence, often tumor relapse. The system described herein possesses an enzyme which can digest components of the tumor matrix and hence aid its own movement. This will enable it to distribute throughout the tumor and hence achieve a better chemotherapeutic effect. Secondly, the covalent linkage of the enzyme to the nanoparticle surface ensures the colocalization of the enzyme and nanoparticle at any time, unlike the systems involving co-injection, where nanoparticles and enzymes can be separated defeating the purpose of enzyme functionalization.

Synthesis of Streptokinase (SK) Functionalized Nanoparticles

Poly-(lactic-co-glycolic acid) nanoparticles are prepared by controlled precipitation from an oil-in-water emulsion stabilized by a surfactant, poly-(vinyl alcohol). The surface of the nanoparticles is stabilized by a block co-polymer PLA-PEG-COOH (PLA-poly-(lactic acid), PEG-poly-(ethylene glycol)). The carboxyl terminal of the PEG is conjugated to an amino group in streptokinase using NHS/EDC cross-linking. The nanoparticles are loaded with either a chemotherapeutic drug such as paclitaxel or a dye for imaging applications. Specific methods are described below.

Synthesis of Nanoparticles:

Poly-(lactic-co-glycolic acid) (PLGA) (32 mg) and paclitaxel (5 mg) or coumarin-6 (250 mcg) were dissolved in 1 mL chloroform and added to 8 mL 2.5% w/v poly-(vinyl alcohol) (PVA) solution in water. This mixture was homogenized with a probe sonicator (20-24 watts) for 5 minutes over an ice bath. 8 mg of diblock co-polymer consisting of poly-(lactic acid) and carboxyl terminal functionalized poly-(ethylene glycol) (PLA-PEG-COOH) was dissolved in 200 mcL of chloroform and added to this emulsion. The formulation was stirred overnight at 25° C. to evaporate chloroform. The precipitated nanoparticles were washed thrice with 30 mL distilled water to remove excess PVA and unbound PLA-PEG-COOH. The nanoparticles (blank NP) were then lyophilized for 48 hours and stored at −20° C.

Conjugation of Streptokinase to Nanoparticles:

Nanoparticles, hence obtained, were dispersed in 1 mL distilled water. Sulfo-N-hydroxy succinimide (Sulfo NHS) and 1-Ethyl-3-(3-dimethyl aminopropyl carbodiimide) (EDC) were added to the dispersion. The molar ratios of sulfoNHS or EDC to PLA-PEG-COOH were 10:1. After 5 hours, streptokinase (SK) (60 units/mg nanoparticles) was added to the mixture and the reaction was allowed to occur overnight. The nanoparticles were washed thrice with distilled water and lyophilized for 48 hours. They were stored at −20° C.

Alternate Conjugation Strategies:

SK may also be conjugated to PLA-PEO-COOH (PEO=poly-(ethylene oxide)) instead of PLA-PEG-COOH. Similarly, other functional groups (e.g., sulfhydryl or amino) may be used.

Particle Size and Zeta Potential:

Dynamic light scattering was used to analyze particles size and zeta potential via Beckman Coulter Delsa Nanoparticle analyzer (see Table 1 below).

TABLE 1

| Nanoparticles | Size (nanometers) | Zeta Potential (millivolts) |
| --- | --- | --- |
| Blank | 201.4 | −24.68 |
| Streptokinase | 236.8 | −24.05 |

Estimation of Conjugation Efficiency:

The amount of streptokinase conjugated to the nanoparticles was analyzed by ThermoScientific BCA protein assay kit (see Table 2 below). Briefly, nanoparticle suspension was prepared in pH 7.4 phosphate buffered saline and incubated with the working reagent for 30 minutes. The nanoparticles were separated by centrifugation at 14,000 RPM for 15 minutes and the resulting supernatant was analyzed by colorimetric assay.

Figure 4:
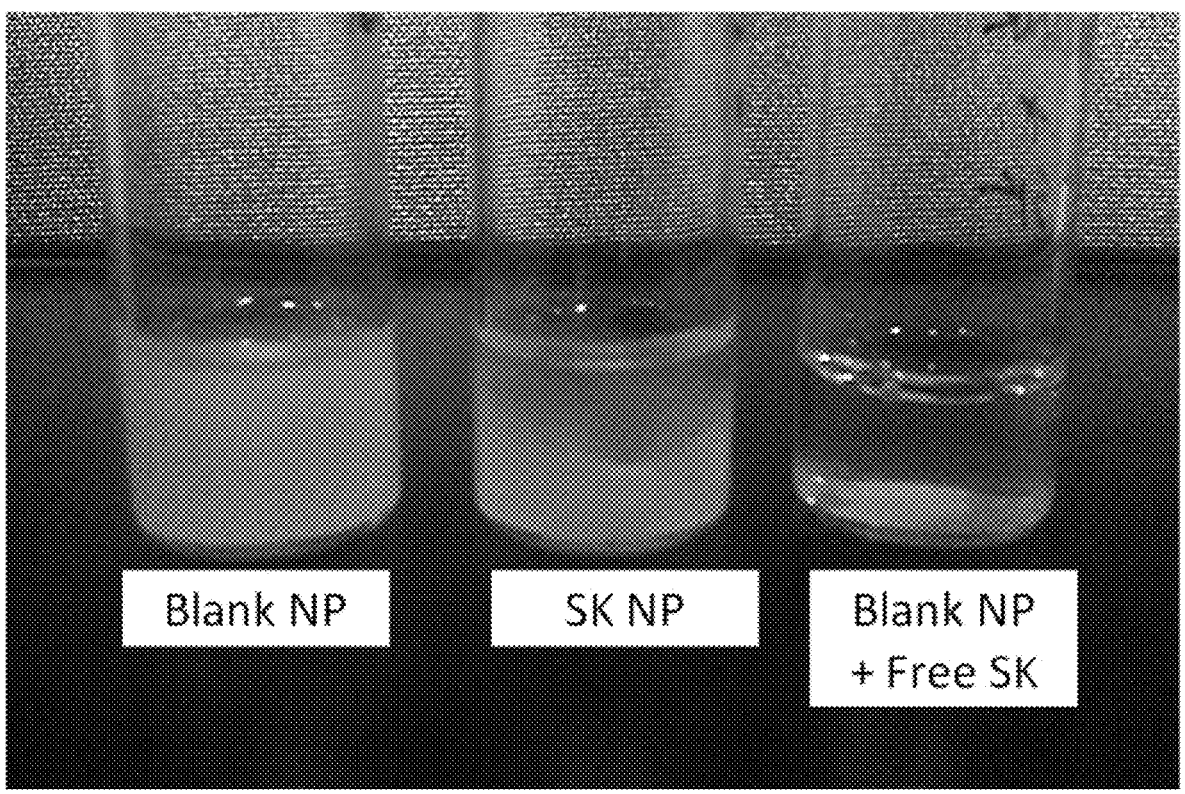
FIG. 4. The effect of streptokinase conjugation: blank NP, SK NP and blank NP+free SK are shown. Nanoparticles were incubated with plasminogen initially and then added to pre-formed fibrin gel. The picture shows migration of the different nanoparticles through the gel. Blank NP did not migrate while SK NP and blank NP+free SK migrated through the gel.

The amount of active SK was measured by incubating the nanoparticles with human plasminogen and D-Val-Leu-Lys-p-nitroanilide dihydrochloride (VALY) for 30 minutes (see Table 2 below). VALY is a substrate of plasmin and upon reaction produces p-nitroanilide which can be analyzed by colorimetry. Various concentrations of free SK with the same concentration of plasminogen and VALY were used as standards in this assay. The effect of streptokinase conjugation is shown in FIG. 4.

TABLE 2

| Parameter | Method | Result |
| --- | --- | --- |
| Fraction of SK conjugated | Bicinchoninic assay (BCA) | 98.17% |
| Fraction of SK active | Plasmin test | 6.80% |

Figure 6A:
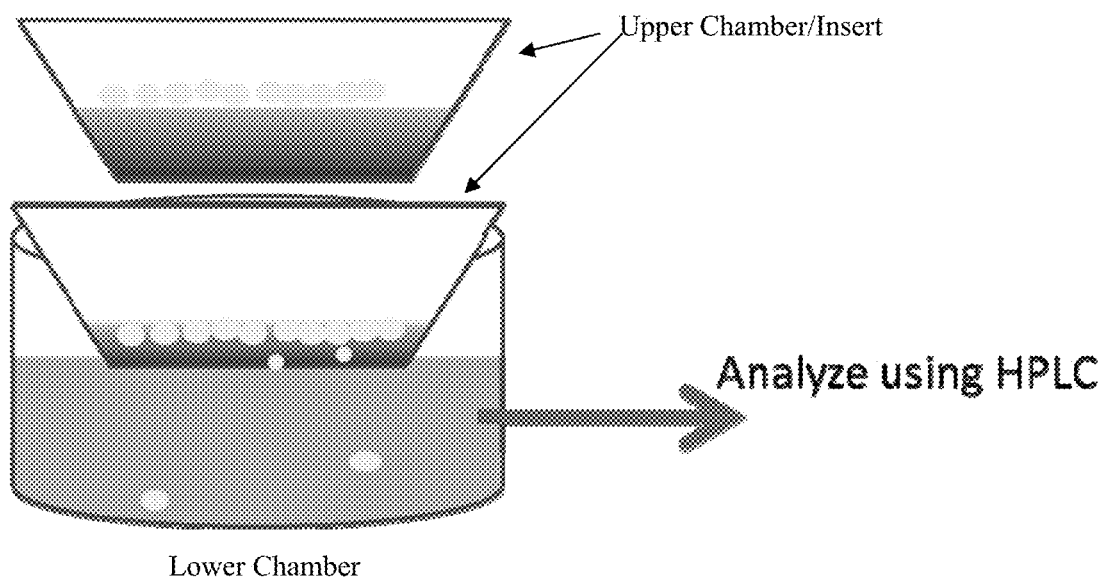
FIGS. 6A-B.
Figure 6B:
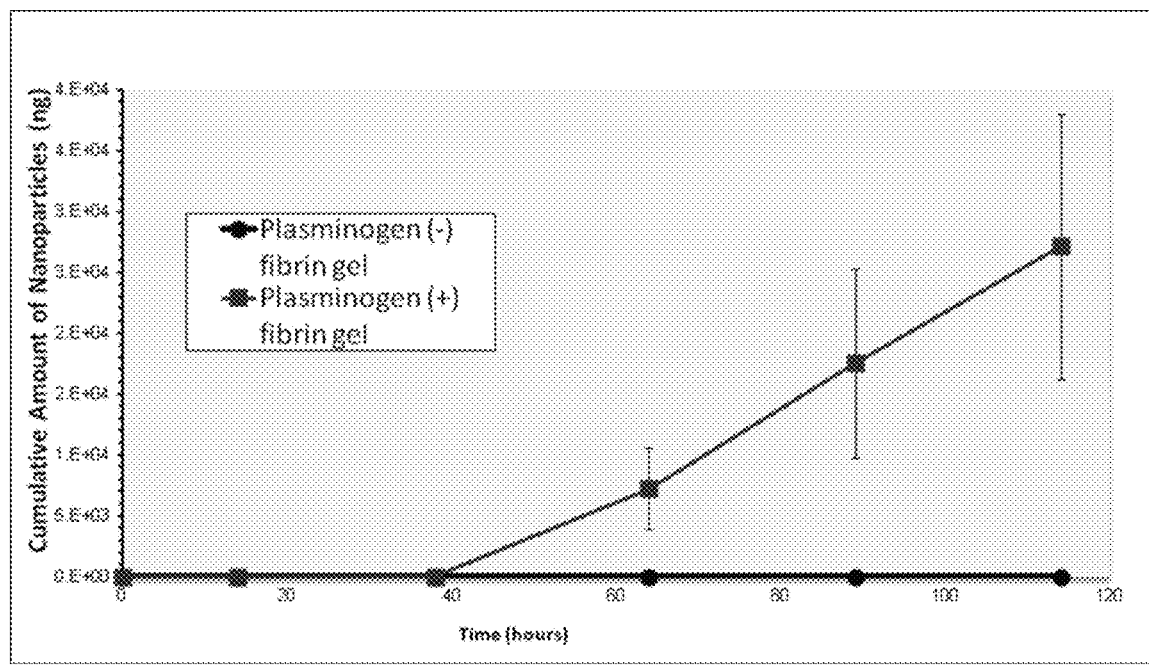

Rate of Nanoparticle Migration Through Fibrin Gels:

An aqueous solution (500 mcL) of bovine fibrinogen (3 mg/mL), human thrombin (1 IU/mL) and sodium chloride (0.9% w/v) was added to six inserts of a 12-well transwell plate. The solution was allowed to gel overnight at 37° C. On the next day, 1 mg SK nanoparticles loaded with paclitaxel, dispersed in 100 mcL distilled water and incubated with 0.1 U human plasminogen for 2 hours, were added to the upper chamber in triplicates. As streptokinase acts through endogenous plasminogen present in the human body, these in vitro studies included a plasminogen incubation step. Simultaneously, the same amount of SK nanoparticles without plasminogen, were added to the other three inserts as a control. The lower chambers were then filled with 1 mL distilled water. At different time points, 500 mcL was removed from the lower well and lyophilized. The product obtained on lyophilization was extracted with methanol and analyzed by HPLC for paclitaxel content. An illustration of the experimental design is shown in FIG. 6A and results are shown in FIG. 6B.

Cell Uptake Study:

Tumors often show nests of cells separated from each other by ECM. Hence the drug must diffuse through the fibrotic tissue to reach the cells. The ability of SK functionalized NPs to by internalized by cells that are separated from the NPs by a fibrin gel barrier was investigated as described below.

Figure 5A:
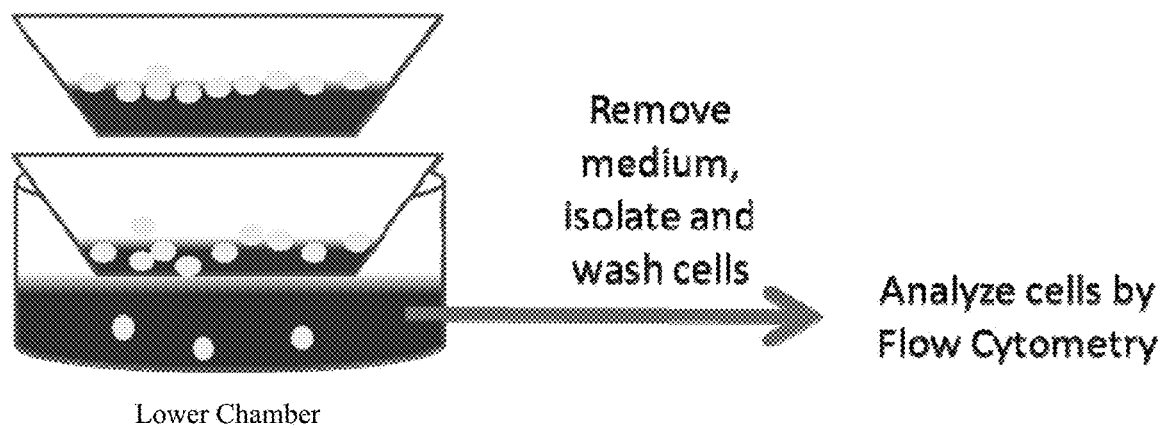
FIGS. 5A-B.
Figure 5B:
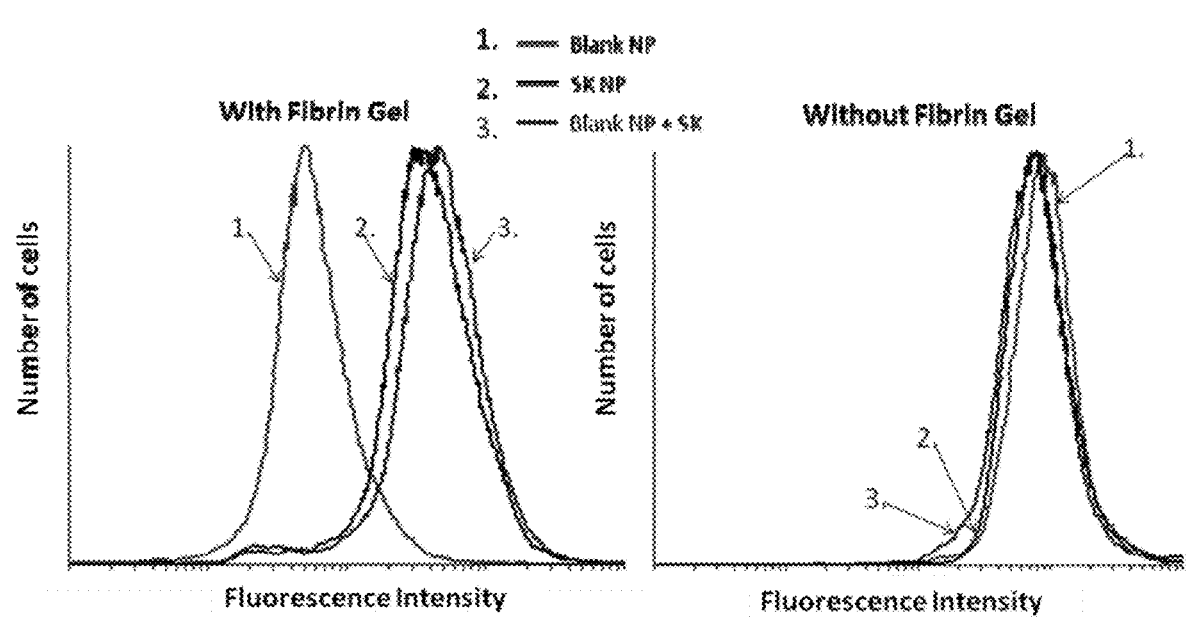

A549 cells (50,000 cells per well) were seeded in the lower chambers of a 6-well transwell plate and allowed to adhere for 24 hours in F12K media with 5% fetal bovine serum and 1% antibiotics. An aqueous solution (500 mcL) of bovine fibrinogen (3 mg/mL), human thrombin (1 IU/mL) and sodium chloride (0.9% w/v) was added to the upper chambers and allowed to gel overnight. On the next day, 1 mg SK nanoparticles loaded with coumarin-6 dispersed in 100 mcL of distilled water and incubated with 0.1 U human plasminogen for 2 hours was added to the top of the gel in duplicates. Blank nanoparticles alone and blank nanoparticles with free SK, treated similarly, acted as negative and positive controls respectively. After 24 hours, media from the lower chambers was discarded and the cells were collected, washed and analyzed by flow cytometry for coumarin-6 uptake. An illustration of the experimental design is shown in FIG. 5A and results are shown in FIG. 5B.

Intra-Tumoral Distribution of Nanoparticles:

A xenograft model is being used to study the in-vivo distribution of nanoparticles in tumors. A549 cells (one million) will be injected subcutaneously in SCID beige mice and the resultant tumors will be allowed to grow to ~700 mm³. 1 mcL of a 3 mg/mL dispersion of SK nanoparticles loaded with a near infra-red dye and incubated with human plasminogen will be injected intra-tumorally at a rate of 0.1 mcL/min. SK nanoparticles at the same concentration without human plasminogen incubation will act as a control. SK is unable to activate murine plasminogen rendering SK ineffective in the absence of human plasminogen. The animals will be imaged using Xenogen live animal imaging at various time points. At the final time point, animals will be sacrificed and the tumors excised. Following sectioning, tumors will be observed under the microscope.

Greater intra-tumoral distribution of SK nanoparticles with human plasminogen compared to that of the controls may be observed.

Pharmacokinetic Studies:

An in-vivo model similar to the one described above will be used for pharmacokinetic experiments. Mice will be injected intravenously with coumarin-6 loaded SK nanoparticles with or without plasminogen. Mice will be euthanized at different time points and key organs including the tumors will be analyzed for the coumarin-6 content.

Nanoparticles with a targeting ligand (targeted nanoparticles) may accumulate and be retained in tumors better than those without the targeting ligand (non-targeted nanoparticles). Various targeting ligands (e.g. folic acid, CREKA peptide, transferrin, or EGFR targeting peptide,) may be used.

Efficacy Studies:

In order to test the efficacy of the formulation, targeted SK nanoparticles loaded with paclitaxel and incubated with human plasminogen will be injected intravenously in mice bearing xenograft tumors. SK nanoparticles alone will act as a control. The growth of the tumor will be monitored over 6-8 weeks to establish the efficacy of this formulation.

Nanoparticle Cargo:

Present studies have been performed with paclitaxel (chemotherapeutic agent) and coumarin-6 (fluorescent dye). As described herein, other therapeutic agents (e.g. anti-cancer agents) or imaging agents may be used (e.g., SDB5491, H.W. Sands Corp. (near infra-red dye)). For example, silicate pro-drugs of paclitaxel may be used to improve loading and release capabilities from the nanoparticles.

NPs described herein may also be used for the treatment of myocardial infarction, wherein streptokinase could act as a therapeutic agent. Additionally, the NPs could also be loaded with an imaging agent (e.g., SDB5491) and used for diagnostic purposes.

Example 3

Methods

Synthesis of Streptokinase Functionalized Nanoparticles (SK NP).

Poly-(lactide-co-glycolide) (PLGA) (Lactel Absorbable Polymers, USA) nanoparticles loaded with paclitaxel, coumarin-6 or SDB5491 were synthesized by a solvent evaporation technique. These nanoparticles were surface functionalized with a carboxyl terminated 10K-3.4K diblock co-polymer of poly-(lactide) (PLA) and poly-(ethylene glycol) (PEG) (Laysan Bio Inc. USA) and were synthesized as described by Patil, Y. B., et al., *Single-step surface functionalization of polymeric nanoparticles for targeted drug delivery*. Biomaterials, 2009. 30(5): p. 859-66.

For streptokinase conjugation, the nanoparticles were dispersed in deionized water (20 mg/mL). Catalysts, N-hydroxy sulfo-succinimide (sulfo-NHS) (Sigma Aldrich, USA) and 1-Ethyl-3-[3-dimethylaminopropyl] carbodiimide hydrochloride (EDC) (Sigma Aldrich, USA) were added to this dispersion. A molar ratio of 10:1::catalysts:block co-polymer was maintained. After 2 hours, streptokinase (Sigma Aldrich, USA, product #S3134) (molar ratio 1:1000::SK:block co-polymer) was added to the reaction mixture. The reaction was allowed to continue for 8 hours. Unreacted catalysts and SK were separated from the nanoparticles by centrifugation. The recovered nanoparticles were lyophilized and stored at −20° C.

Physicochemical Characterization of SK NPs.

The size and zeta potential of blank NPs or SK NPs were measured using Delsa Nano® size and zeta potential analyzer (Beckmann Coulter, USA) by dispersing the nanoparticles in deionized water.

A bicichoninic protein assay (BCA) kit (Thermo Fischer, USA) was used to determine the amount of protein conjugated to the surface of nanoparticles.

To determine the amount of active streptokinase, a plasmin estimation assay was used. Known amounts of streptokinase or SK NPs were incubated with an excess of human plasminogen (EMD Millipore, USA, product #528175) and D-Val-Leu-Lys 4-nitroanilide dihydrochloride plasmin substrate (Sigma Aldrich, USA, product #V0882). After 30 minutes, the amount of nitroaniline was measured using ELx800 absorbance microplate reader (BioTek Co., USA) at 405 nm.

Rate of Migration of Nanoparticles Through Fibrin Gels.

An aqueous solution of bovine fibrinogen (3 mg/mL) (Sigma Aldrich, USA, product #F8630), bovine thrombin (1 IU/mL) (Sigma Aldrich, USA, product #T4648) and sodium chloride (0.9% w/v) was prepared. 0.5 mL of this solution added to top inserts of a 12-well transwell plate. The solution was allowed to gel overnight at 37° C.

On the next day, 1 mg SK nanoparticles loaded with paclitaxel was dispersed in 100 mcL distilled water and incubated with 0.1 IU human plasminogen for 2 hours. As streptokinase acts through endogenous plasminogen present in the human body, these in vitro studies included a plasminogen incubation step. This activated mixture was added to the upper inserts in triplicates. Simultaneously, the same amount of SK nanoparticles without plasminogen incubation was added in triplicate to the other inserts as a control. The lower wells were then filled with 1 mL distilled water. At set time points, 500 mcL was sampled from the lower well and replaced with fresh water. The aliquots obtained were lyophilized and extracted with methanol and analyzed by HPLC for paclitaxel content.

Cell Uptake Study.

Human lung cancer A549 cells (50,000 cells per well) were seeded in a 6-well transwell plate and allowed to adhere for 24 hours in F12K media with 5% fetal bovine serum and 1% antibiotics. Fibrin gels were formed in the upper inserts of the transwell plates as described before. On the next day, 1 mg SK nanoparticles loaded with coumarin-6 dispersed in 100 mcL of distilled water and incubated with 0.1 IU human plasminogen for 2 hours was added to the top of the gel in triplicates. Blank nanoparticles alone and blank nanoparticles with free SK, treated similarly, acted as negative and positive controls respectively. After 24 hours, media from the lower wells was discarded and the cells were collected, washed and analyzed by flow cytometry (FACSCalibur, BD Biosciences, USA). SK NPs, blank NPs and blank NPs with free SK were also incubated with cells alone, to compare cell uptake in the absence of fibrin gels.

In Vivo Intratumoral Distribution of Nanoparticles.

One million A549 cells transfected with firefly luciferase gene (A549-luc[+] cells) dispersed in phosphate buffered saline were injected in sub-cutaneously in the mammary fat pad of female SCID mice (Charles River Labs, USA). The tumor growth was monitored using digital calipers. Tumor volume was calculated as $V=0.51*w^2$ (where l=length and w=width). When tumors reached a volume of 400 $mm^3$, the animals were randomly assigned to a control or treatment group.

On the day of the experiment, a dispersion of SK NPs loaded with SDB5491 was prepared in deionized water at a concentration of 3 mg/mL. This dispersion was incubated with either human plasminogen (12 IU/mL) or diluted with equivalent volume of DI water for two hours. The particles incubated with plasminogen served as a treatment group and those incubated with DI water served as a negative control. SK is unable to activate murine plasminogen rendering SK ineffective in the absence of human plasminogen.

Before injection the mice were anesthetized using isoflurane gas. The nanoparticle dispersion (1 mcL) was injected in the tumor using stereotactic injection at a rate of 0.1 mcL/min. The mice were then imaged in the epi-fluorescence mode using Xenogen IVIS 100 imaging system. The experimental parameters are summarized in Table 3.

TABLE 3

List of experimental parameters used in live animal imaging

| Parameter | Value |
|---|---|
| Excitation wavelength | 745 nm |
| Emission wavelength | 820 nm |
| Field of view (FOV) | B |
| f-stop | 8 |
| Binning | 2 |
| Exposure time | Auto |

The animals were imaged at times 0, 3, 24 and 48 hours post-injection. The data was then analyzed using Live Animal Imaging software. A line profile was obtained for the intensity of emitted light as a function of distance from the point of injection in the tumor. The distance at which this intensity went below 10% of the point of injection was measured.

Results

Physicochemical Characterization of SK NPs.

The particle size and zeta potential was measured using dynamic light scattering. The amount of streptokinase on the surface of the nanoparticles was measured using a BCA kit. The amount of active streptokinase was measured using a plasmin activity measurement kit. These results are summarized in Table 4.

TABLE 4

Physicochemical characterization of Blank and SK NPs

| Nanoparticles | Blank NP | SK NP |
|---|---|---|
| Size | 201.4 nm | 236.8 nm |
| Zeta potential | −24.68 mV | −24.05 mV |
| Amt. of SK conjugated | — | 2.98 mcg/mg NP |
| Amt. of SK active | — | 0.202 mcg/mg NP |

Rate of Migration of Nanoparticles Through Fibrin Gels.

Figure 7:
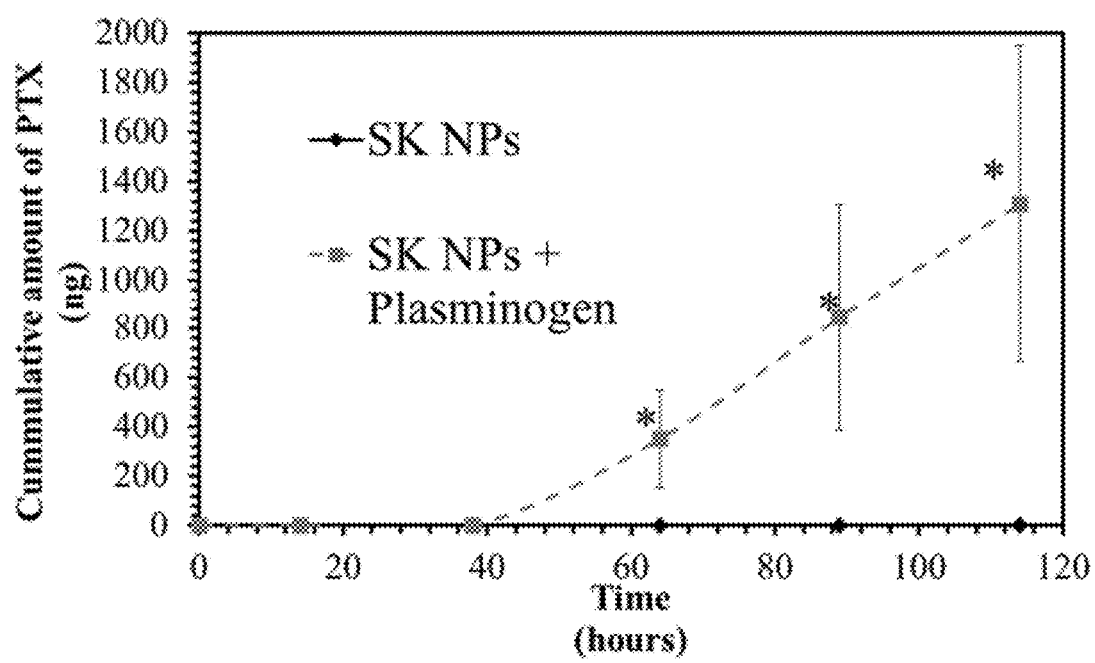
FIG. 7. Rate of migration across fibrin gels. Nanoparticles loaded with paclitaxel and functionalized with SK were placed on top of fibrin gels in transwell inserts. Nanoparticles in the presence of human plasminogen served as treatment group and in the absence of the same served as controls. Plasminogen treated SK NPs showed a significantly higher rate of migration across fibrin gels as compared to the non-treated counterparts. * indicates p<0.1.

Fibrin gels were formed in-situ in the upper wells of transwell plates. SK NPs loaded with paclitaxel, incubated with human plasminogen (treatment) or without plasminogen incubation (control), were carefully added to the top of these gels. The bottom wells were aliquoted and the concentration of paclitaxel was measured using HPLC. The results are summarized in FIG. 7.

Upon plasminogen incubation, the activated SK NPs had a much higher rate of migration than the inactivated particles. There was a statistically significant increase in the amount of paclitaxel accumulation in the bottom chamber as time progressed. There was a lag in the appearance of paclitaxel in the bottom chamber. This lag corresponded to the time required for the activated nanoparticles to digest the fibrin gels and reach the bottom of the insert. This indicated the degree of impermeability of these gels.

Cell Uptake Study.

Blank NPs, blank NPs with free SK or SK NPs were incubated A549 cells either directly or separated by fibrin gels. After 24 hours, the nanoparticles were separated from the cells and the fluorescence intensity in the cells was analyzed using flow cytometry. The results are summarized in FIG. 8.

As indicated in FIG. 8A, there was a significant reduction in the fluorescent intensity of the cells in the presence of fibrin gels. This indicates the resistance provided by the fibrin gel nanoparticle transport. The lack of efficient migration of NPs across the fibrin gels impeded their availability for cellular uptake. This resulted in a reduction in mean fluorescence intensity. However, SK NPs degraded the fibrin gels and reached the bottom of the transwell plates. Hence, the fluorescence intensities were comparable in the presence and absence of fibrin gels (FIG. 8B). The positive control also showed similar results to the SK NPs (FIG. 8C).

In Vivo Intratumoral Distribution of Nanoparticles.

A549-luc$^+$ were injected subcutaneously in SCID mice. The tumors were allowed to grow to 400 mm$^3$. SK NPs with or without plasminogen incubation were injected intratumorally in these mice. The distribution of NPs was monitored using Xenogen IVIS living image. FIG. 9 shows a representative image of the spread of the nanoparticles as a function of time. SK NPs without human plasminogen incubation are limited in their distribution and form a small spot at the site of injection. This spot is maintained up to 48 hours post-injection (FIG. 9A). The intratumoral distribution of the nanoparticles is significantly thwarted. However, upon activation by human plasminogen, the nanoparticles show a wider distribution in the tumor matrix (FIG. 9B).

Figure 10:
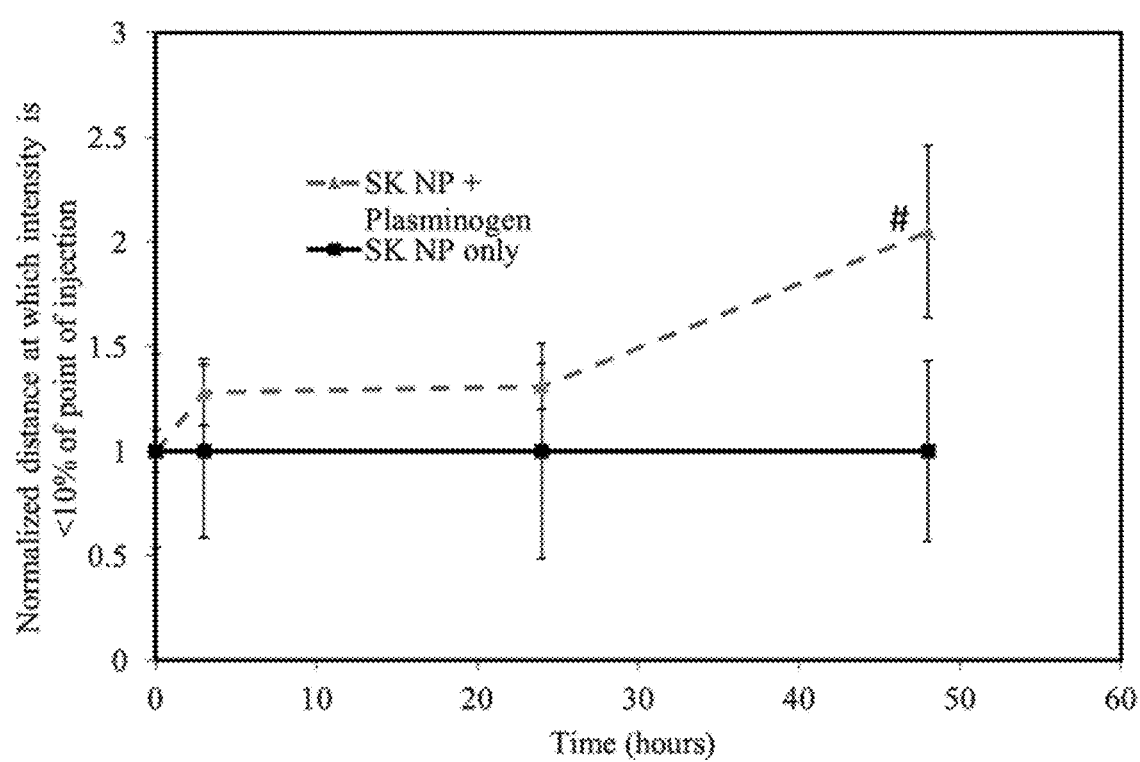
FIG. 10. Quantification of intratumoral distribution of nanoparticles. The images obtained from the IVIS imaging were analyzed using Live Animal Imaging software. A line profile was generated quantifying the fluorescence intensity as a function of distance from the point of injection. The distance at which this intensity fell below 10% of point of injection was measured. This value was normalized to the value obtained for the controls. In terms of this distance, treated group showed a 2-fold increase at 48 hours post injection. This difference was statistically significant. # indicates p<0.05.

These results are quantified in FIG. 10. The distance at which the fluorescence intensity falls below 10% of the point of injection is significantly higher for the plasminogen-activated nanoparticles as compared to the inactivated nanoparticles. This spread is ~2 fold higher at 48 hours post injection.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A nanoparticle comprising a polymer and one or more units of formula (I):

A-B-C-D      (I)

wherein A is poly-lactic acid or poly-(lactic-co-glycolic acid); B is poly-(ethylene glycol); C is a linking group and D is one or more moieties independently selected from tissue plasminogen activator (tPA) and recombinant tissue plasminogen activator (r-tPA), wherein the r-tPA is alteplase or reteplase.

2. The nanoparticle of claim 1, wherein A is embedded or partially embedded in the polymer.

3. The nanoparticle of claim 1, wherein A is poly-lactic acid.

4. The nanoparticle of claim 1, wherein A is poly-(lactic-co-glycolic acid).

5. The nanoparticle of claim 1, wherein the linking group is a direct bond or —OC(=O)(CH$_2$)$_n$C(=O)O—, wherein n is 1-10.

6. The nanoparticle of claim 1, wherein the linking group is derivable from carboxy and is —C(=O)—.

7. The nanoparticle of claim 1, wherein the linking group is derivable from maleimide and is:

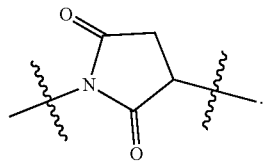 [SMILES: *C1CC(=O)N(*)C1=O]

8. The nanoparticle of claim 1, wherein D is tPA.
9. The nanoparticle of claim 1, wherein D is reteplase.
10. The nanoparticle of claim 1, wherein D is alteplase.
11. The nanoparticle of claim 1, wherein the polymer is selected from poly-(lactic-co-glycolic acid), polyanhydride, poly sulfonamide, alginate, chitosan, polyethyleneimine, polyethylene glycol, poly-L-lysisne, polyglutamic acid, cellulosic derivatives, and acrylic acid based polymers.
12. The nanoparticle of claim 1, wherein the polymer is poly (lactic-co-glycolic acid).
13. The nanoparticle of claim 1, further comprising one or more therapeutic agents.
14. The nanoparticle of claim 13, wherein the one or more therapeutic agents is an anti-cancer agent.
15. The nanoparticle of claim 14, wherein the anti-cancer agent is selected from All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, a tyrosine kinase inhibitor, an antibody, trastuzumab, bevacizumab and pharmaceutically acceptable salts thereof, or combinations thereof.
16. The nanoparticle of claim 1, further comprising one or more imaging agents independently selected from coumarin-6, SDB5491, rhodamine derivatives, cy5.5, radiolabels for PET imaging and diagnostic agents suitable for MM imaging.
17. A pharmaceutical composition comprising a nanoparticle as described in claim 1 and a pharmaceutically acceptable carrier.
18. A compound of formula (I):

A-B-C-D      (I)

wherein A is poly-lactic acid or poly-(lactic-co-glycolic acid); B is poly-(ethylene glycol); C is a linking group and D is one or more moieties independently selected tissue plasminogen activator (tPA) and recombinant tissue plasminogen activator (r-tPA), wherein the r-tPA is alteplase or reteplase.

19. The compound of claim 18, wherein the linking group is a direct bond or —OC(=O)(CH$_2$)$_n$C(=O)O—, wherein n is 1-10.

20. The compound of claim 18, wherein D is tPA.

21. The compound of claim 18, wherein D is reteplase.

22. The compound of claim 18, wherein D is alteplase.

23. A method for treating myocardial infarction in an animal, comprising administering to the animal a nanoparticle as described in claim 1.

24. A method for treating cancer in an animal, comprising administering to the animal a nanoparticle as described in claim 14.

* * * * *

UNITED STATES PATENT AND TRADEMARK OFFICE
CERTIFICATE OF CORRECTION

PATENT NO. : 10,967,062 B2
APPLICATION NO. : 15/841145
DATED : April 6, 2021
INVENTOR(S) : Panyam et al.

Page 1 of 1

It is certified that error appears in the above-identified patent and that said Letters Patent is hereby corrected as shown below:

In the Claims

Column 22, Line 31, Claim 11, please delete "poly sulfonamide" and insert -- polysulfonamide --;

Column 22, Line 57, Claim 16, please delete "for MM" and insert -- for MRI -- therefor.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*